(12) United States Patent
Cherian

(10) Patent No.: US 6,548,071 B1
(45) Date of Patent: *Apr. 15, 2003

(54) LYOPHILIZATE OF LIPID COMPLEX OF WATER INSOLUBLE CAMPTOTHECINS

(75) Inventor: Mathew Cherian, Albuquerque, NM (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/871,558

(22) Filed: Jun. 10, 1997

Related U.S. Application Data

(63) Continuation of application No. 08/323,081, filed on Oct. 14, 1994, now abandoned.

(51) Int. Cl.⁷ .................................................. A61K 31/44
(52) U.S. Cl. ........................ 424/400; 424/484; 514/283
(58) Field of Search ......................... 514/283; 424/400, 424/484

(56) References Cited

U.S. PATENT DOCUMENTS

| | | | |
|---|---|---|---|
| 4,008,209 A | | 2/1977 | Fujino et al. |
| 4,229,360 A | * | 10/1980 | Schneider et al. ........... 424/199 |
| 4,311,712 A | * | 1/1982 | Evans et al. ................ 424/365 |
| 4,610,868 A | | 9/1986 | Fountain ..................... 424/121 |
| 5,077,057 A | | 12/1991 | Szoka, Jr. ................... 424/450 |
| 5,389,377 A | | 2/1995 | Chagnon .................... 424/450 |
| 5,415,867 A | * | 5/1995 | Minchey et al. ............ 424/450 |
| 5,431,900 A | * | 7/1995 | Bergstein et al. ........... 424/165 |
| 5,552,156 A | * | 9/1996 | Burke ......................... 424/450 |
| 5,616,334 A | * | 4/1997 | Janoff et al. ................ 424/404 |
| 5,834,012 A | * | 11/1998 | Perez-Soler et al. ........ 424/450 |
| 6,090,407 A | * | 7/2000 | Knight et al. ............... 424/450 |

OTHER PUBLICATIONS

Janoff et al., J. of Liposome Research, 452–471 (1993) pp. 460–461.
Hillery, Adv. Drug Delivery Reviews, 345–363 (1997) abstract pp. 346, 350 (Table 2), 356.
Hope et al., Advanced Drug, Delivery Reviews, 24 (1997) (345–363), abstract.
Deamer, D.W.,et al. "*Liposome Preparation: Methods and Mechanisims*" pps. 37–51.
Burke et al., "Liposomal Stabilization of Camptothecin's Lactone Ring", J.Am.Chem.Soc. 1992, 8318–8319 (Oct.).
Burke et al., "Lipid Bilayer Partitioning and Stability of Camptothecin Drugs", Biochemistry 1993, 5352–5364 (May).
Sugarmen, CA 124:332078, 1996.*
CA 117:103,369 "Preclinical studies of DNA Topoisomer–ase I–targeted 9–amino and 10,11–methylenedioxy Camptothecins" Giovanella, et al. (1991).*

* cited by examiner

*Primary Examiner*—Jeffrey Mullis
(74) *Attorney, Agent, or Firm*—Thompson Hine LLP

(57) ABSTRACT

A pharmaceutical composition comprising a lyophilizate of non-liposomal complex of a water insoluble camptothecin and a phospholipid, said lyophilizate additionally containing a pharmaceutically acceptable lyophilization excipient, wherein the weight ratio of said camptothecin to said phospholipid in said composition is about 1:80 to 1:5.

21 Claims, No Drawings

LYOPHILIZATE OF LIPID COMPLEX OF WATER INSOLUBLE CAMPTOTHECINS

This is a continuation of U.S. patent application Ser. No. 08/323,081, filed Oct. 14, 1994 now abandoned.

BACKGROUND OF THE INVENTION

The present invention relates to a pharmaceutically acceptable dosage form for water insoluble camptothecins and, more particularly 9-amino 20(S)-camptothecin (hereafter 9-AC) and 9-amino-20(R)-camptothecin which can be reconstituted and administered to a patient intravenously or subcutaneously or formulated for oral use in the treatment of cancer and other diseases.

Camptothecin and analogues thereof, display antitumor activities against colon cancer, leukemia, and experimentally transplanted carcinoma such as leukemia L-1210 in mice or Walker 256 tumors in rats. See Potsmiesel, M., DNA Topoisomerases in Cancer. Camptothecin is a pentacyclic alkaloid including a characteristic fused 5-ring system of quinoline (rings A and B), pyroline (ring C), α-pyridone (ring D) and a six-membered lactone (ring E). The intact lactone ring, ring E, and hydroxyl group at position 20 have been found to be essential to its antitumor activity.

Studies of camptothecin analogs have suggested a correlation between the compound's ability to induce DNA breakage and its antitumor activity. It has a unique mechanism of action which produces DNA damage in the presence of topoisomerase I, a monomeric enzyme that is capable of altering DNA topology in eukaryotic cells. Topoisomerase I binds to the DNA to allow the double helix to unwind and subsequently reseals the break before dissociating from the DNA strand. Camptothecin is believed to bind to and stabilize a covalent DNA-topoisomerase I complex in which one strand of the DNA helix is broken and thereby prevent the DNA from recombining.

The therapeutic use of camptothecin and its analogs has been severely limited by their poor water solubility and high toxicity. A number of attempts have been made to reduce the toxicity of camptothecin without reducing its antitumor activity through the development of derivatives. Camptothecin derivatives substituted at the 5-, 7-, 9-, 10-, and 11-positions have been investigated. At least three camptothecin derivatives are in various stages of clinical development, namely: 7-ethyl-[14-(1-piperidino)-1-piperidine] carbonyloxycamptothecin (CPT-11); 20-(S)-camptothecin; 10-[(dimethylamino)methyl]-4-ethyl-4,9-dihydroxy-1H-pyrano[3',4':6,7]indolizino[1,2-b]quinoline-3,14(4H,12H)dione monohydrochloride (topotecan hydrochloride); and 9-amino-20(s)-camptothecin.

9-AC is quite water insoluble (0.002 mg/ml). This makes it difficult to formulate as a sterile, storage stable, dosage form. In studies carried out by the National Cancer Institute (NCI) 9-AC was formulated in an organic solvent, dimethylacetamide (DMA), to overcome the solubility limitations of the drug. The NCI formulation consists of 5 mg of 9-AC in 1 ml of DMA. At the point of use, the product is diluted using a diluent consisting of polyethylene glycol 400, USP, and phosphoric acid. The diluent is added to the NCI formulation in an amount of 49 ml diluent to 1 ml formulation.

The NCI formulation has drawbacks which make the formulation inconvenient for commercial use. Because the DMAC attacks rubber stoppers, the product cannot be supplied in stoppered vials and must be supplied in ampules. Ampules are inconvenient to use because they must be scored and broken to open them and this presents some risk of injury and contamination to workers. Additionally, glass chips in the product from breaking open the ampules need to be filtered out.

DMA is not a desirable vehicle for intravenous (IV) administration and a potential source of toxic side effects. DMA has an $LD_{50}$ value of 5.4 ml/kg, which is a factor which also must be considered in administering the drug.

Another approach to designing camptothecin dosage forms which has been investigated involves the use of liposomes. T. G. Burke et al. in Biochemistry 1993, 32, 5352–64 (1993) suggest using liposomes as a drug delivery system for camptothecin. Burke et al. found that camptothecin binds with dimyristoylphosphatidylglycerol (DMPG) lipids and dimyristoylphosphatidylcholine (DMPC) lipids and is stable in both DMPC and DMPG liposome bilayers. They postulate that the lactone ring penetrates the liposome layer. The liposome-associated camptothecin showed stabilization of the lactone ring.

No satisfactory pharmaceutically acceptable formulation of 9-AC is currently available for administration to humans. There is a need for a stable pharmaceutical dosage form which may be conveniently administered to a cancer patient while retaining the structural elements that are essential for 9-AC's pharmacological activity.

SUMMARY

It is an object of the present invention to provide a pharmaceutically acceptable dosage form of 9-AC or another water insoluble camptothecin. It is another object of the present invention to provide lipid complexes of 9-AC and other water insoluble camptothecins. It is still another object of the invention to provide lyophilizates of three lipid complexes. The lyophilizate can be reconstituted with water, saline, or another electrolyte to give a colloidal dispersion for intravenous or subcutaneous administration or can be formulated into a paste or filled into a soft gelatin or hard gelatin capsule for oral administration. Previously, camptothecins have not been administered subcutaneously because they are necrotic. However, it appears that the lipid complex may sufficiently slow the release of water insoluble camptothecins that subcutaneous administration is possible.

While the invention will hereafter be described with respect to the preparation of lipid complexes and lyophilizates of lipid complexes of 9-AC, those skilled in the art will appreciate that the methods taught herein are also applicable to the preparation of lipid complexes and lyophilizates of other camptothecins which are considered water insoluble such as camptothecin itself.

In accordance with the present invention, a lyophilizate of a phospholipid complex of 9-AC is prepared which can be reconstituted with pharmaceutically acceptable aqueous diluent such as water for injection and which, in comparison to solutions of 9-AC in dimethylacetamide, is less toxic, more stable and particularly importantly, its formulation and administration are not limited by the solubility of 9-AC.

In accordance with the invention, the lyophilizate is prepared by a process comprising the steps of preparing a solution of 9-AC in a first organic solvent, preparing a solution of a phospholipid in a second organic solvent, mixing the phospholipid solution and the 9-AC solution, adding water to the mixed solutions to cause formation of a lipid complex of 9-AC, removing the first and second organic solvents to provide a dispersion of the lipid complex in water as an aqueous phase, dissolving a pharmaceutically acceptable excipient in the aqueous phase of the dispersion, and lyophilizing the dispersion of the lipid complex to form a lyophilizate. This lyophilizate forms a colloidal dispersion when reconstituted with a physiologically acceptable aqueous diluent.

In accordance with a preferred embodiment of the present invention, the lyophilizate is prepared by a method comprising the steps of forming a concentrated solution of 9-AC in dimethyl sulfoxide, forming a concentrated solution of the phospholipids DMPC and DMPG in chloroform, mixing the phospholipid solution and the 9-AC solution, adding an aqueous solution such as water for injection to form the lipid complex of 9-AC and provide a dispersion of the lipid complex in water as an aqueous phase, sparging and diafiltering the dispersion to remove the solvents, reducing the particle size of the dispersion of the lipid complex, adding an aqueous solution of mannitol as a pharmaceutically acceptable lyophilization excipient to the dispersion, and lyophilizing, wherein a lyophilizate is obtained which upon reconstituting with water provides a colloidal dispersion of a 9-AC lipid complex.

In accordance with a further embodiment of the present invention, a lyophilized composition containing 9-aminocamptothecin or another water insoluble camptothecin is provided which comprises 9-AC, a phospholipid and a pharmaceutically acceptable lyophilization excipient.

DETAILED DESCRIPTION OF THE INVENTION

The term "water insoluble camptothecin" as used herein means camptothecin or another pentacyclic alkaloid having the aforementioned characteristic fused 5-ring system of camptothecin having a solubility in water which is less than 0.01 mg/ml at 23° C.

The term "lipid complex" is an art recognized term. Lipid complexes are characterized by a noncovalent bond between the lipid and the camptothecin which is observed as a phase change in differential scanning calorimetry.

The term "pharmaceutically acceptable aqueous diluent" as used herein refers to water for injection, saline, and other known aqueous vehicles.

The term "lyophilization excipient" refers to a. substance which is added to a solution prior to lyophilization to enhance characteristics such as the color, texture, strength, and volume of the cake. Examples of lyophilization excipients are provided below 9-AC has been prepared by reduction of 9-nitrocamptothecin with a reducing agent such as a combination of tin or iron with a mineral acid. (See U.S. Pat. No. 4,604,463 to Miyasaka et al.) The preparation of 9-amino-20(S)-amptothecin and 9-amino-20(R,S)-camptothecin is described in U.S. Pat. Nos. 5,106,742 and 5,225,404. Other water insoluble camptothecins are known in the art and their preparation is described in the literature.

9-Amino-20(S)-camptothecin has a chemical formula of $C_{20} H_{17} N_3 O_4$ and the structure:

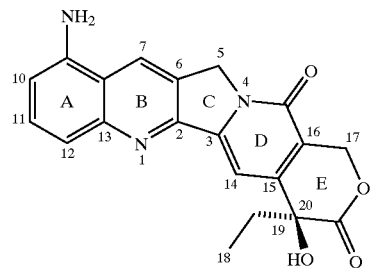

In accordance with the invention a concentrated solution of 9-AC in an organic solvent is prepared. The most typical example of the solvent used to prepare this solution is dimethyl sulfoxide (DMSO). However, other organic solvents such as dimethyl formamide can be used. Useful solvents must form stable solutions with the camptothecin analogue, e.g., the solvent must not interact with, destabilize, and/or deactivate the drug. In addition, the solubility of the camptothecin analogue in the solvent must also be high enough that the camptothecin analogue can be dissolved in amounts sufficiently high to form commercially useful quantities of the lipid complex and the solvent should be capable of being removed easily from an aqueous dispersion of the lipid complex as described hereinafter. Preferably, a solution having a concentration of about 5 to 50 mg/ml, preferably about 20 to 40 mg/ml and most preferably 40 mg/ml camptothecin is used. The concentration may vary depending upon the nature of the solvent and temperature, but it is important to use a concentrated solution of the camptothecin in preparing the liquid/camptothecin complex. This minimizes the amount of solvent that must be removed later in the process, and it also assists in forcing the camptothecin out of solution and into liquid/camptothecin complex formation with the lipid with the addition of water.

The organic solvent used to prepare the solution of the phospholipids should meet similar requirements to those outlined for the camptothecin solvent. It must be compatible with the phospholipids and not destabilize them or the camptothecins. In addition, the lipids should be soluble enough in the solvent so as to be able to introduce enough of the lipid to form the complex yet minimize the amount of solvent that must be removed later. A solvent which can be readily removed from the dispersion of the lipid complex is most preferred. The solvent most typically used to prepare this solution is chloroform or methylene chloride. Typically the concentration of this phospholipid solution will range from about 10 to 250 mg/ml.

Phospholipids are amphipathic in nature, i.e., the molecules have a hydrophobic tail such as a long chain hydrocarbon, and a hydrophilic head. In an aqueous medium, such as water or saline, the tails align with each other, away from the aqueous molecules, while the heads face. outward into the aqueous phase. It is this nature of the phospholipids that makes them very useful for formulating highly insoluble drugs like 9-AC.

The phospholipids used in the invention are selected such that their phase transition temperature is about equal to or below the body temperature or 37° C. and the complex releases the drug in the body. Representative examples of useful phospholipids include synthetic phospholipids DMPC, DMPG, dipalmitoylphosphatidylcholine (DPPC), dipalmitoylphosphatidylglycerol (DPPG), distearoylphos-phatidylcholine (DSPC), or distearoylphos-phatidylglycerol (DSPG), or a combination thereof. Other examples of phospholipids can be found in the *CRC Handbook of Livid Bilayers* by Marsh, M. A., CRC Press (1990). When DMPC and DMPG are used in a ratio of DMPC to DMPG of about 7:3 they mimic the cell membrane.

The lipid solution is added to the 9-AC solution such that the weight ratio of the 9-AC to lipid is about 1:80 to 1:5, preferably about 1:80 to 1:10, more preferably, about 1:60 to 1:10 and still more preferably about 1:45 to 1:25.

In some applications, it has been found desirable to add cholesterol or its hemisuccinate derivatives to the lipid complex. The cholesterol is believed to cause the bilayers to pack more closely and thereby slow the release of the drug. This approach may be particularly desirable with subcutaneous formulations where severe necrosis can result if the drug is delivered too quickly. The cholesterol is added to the phospholipid solution. The cholesterol may be used in an amount of about 0.5 to 15 parts per 100 parts phospholipid.

Once the solvent solutions of the lipids and camptothecin have been mixed, water or an aqueous solution is added rapidly and with stirring for several minutes to the mixture. Addition of the water is believed to cause the 9-AC and the lipid to come out of their respective solvent solutions and complex with each other. The water is preferably added in an amount such that the 9-AC is present in an amount of about 0.05 mg to 0.5 mg per 100 ml water. It is desirable to limit the amount of water to minimize the amount of water which must be removed during the lyophilization process. Higher amounts of water are undesirable because they increase the amount of water that must be removed during the subsequent lyophilization process. It is believed complexation may be complete in about 30 minutes. However, it is desirable to stir the dispersion for about one hour to insure complexation is complete.

The lipid complex dispersion described above, is treated to remove the solvents. Any of a variety of techniques can be used for this purpose. For example, it has been found that the chloroform can be removed if the dispersion is sparged with a gas such as nitrogen. A diafiltration process (also known as a tangential flow filtration process) is used to remove the DMSO. A cartridge of hollow fiber tubes having a pore size of 5 to 150 kilodaltons can be used. A diafiltration cartridge is available from A/G Technology Corporation of Needham, Massachusetts under the tradename XPRESS, which can be used. Other techniques which can be used include centrifugation.

A pharmaceutically acceptable lyophilization excipient is dissolved in the aqueous phase of the dispersion. Mannitol is typically used as the excipient but other excipients which do not interact with the drug or the lipid complex may be used. Sodium or potassium phosphate, citric acid, tartaric acid, gelatin, and carbohydrates such as mannitol, lactose, dextrose, dextran, hetastarch, etc. are common examples of excipients which are also believed to be useful herein. The excipients can be used alone or in combinat ion to provide a cake of good quality which readily disperses in water upon reconstitution.

The excipients are typically added to the dispersion as solutions in water. Again, it is desirable to use concentrated solutions to minimize the amount of water for removal by lyophilization. The amount of the excipient is adjusted in a manner that is well known in the art to provide a cake which does not crack or shrink and is porous so that it readily dissolves and has a good appearance. Mannitol has been found to be useful. Mannitol is added to the dispersion as a solution having a concentration of about 5 to 150 g/ml. Mannitol is added in an amount of about 1 to 100 parts by weight per 1 part 9-AC.

After removing the solvents and adding the excipient, the dispersion is passed through a homogenizer (e.g., a Tekmar rotor/stator homogenizer, Model T25, or a microfluidics submerged jet homogenizer, Model M110Y). As a general rule, the smaller the particle size of the dispersion, the faster the formulation can be dried during the lyophilization cycle. A dispersion having a particle size distribution ranging from about 10 to 500 nm and averaging about 250 nm has been found to be satisfactory for lyophilization. The optimum particle size may vary depending on the mode of administration.

A typical lyophilization cycle useful in accordance with the present invention is provided below. The cycle may be varied depending upon the equipment and facilities available in a manner well known in the art.

The homogenized formulation can be poured into vials of a 5 to 50 ml nominal volume. The vials are placed into a lyophilization chamber at about 5° C. The vial size will usually be selected such that each vial contains a single dosage of the 9-AC. The temperature of the chamber is reduced to −30° C. over a period of one hour after which the temperature is maintained at −30° C. for about four hours. The pressure in the lyophilization chamber is then reduced to 200–250 microns of pressure for the remainder of the cycle. After reducing the pressure in the chamber, the temperature is ramped up to +25° C. over a period of fifteen hours and the product is held at 250C for five hours. The temperature then is ramped up to +40° C. over a period of 20 minutes and held at 40° C. for two hours. The lyophilized product preferably has a final moisture content of less than about 5% and typically about 1 to 2%.

For intravenous or subcutaneous administration, the lyophilizate can be reconstituted using aqueous vehicles such as water, saline or another electrolyte. The lyophilized product with the addition of water provides a colloidal dispersion of the lipid complex in an aqueous solution of the excipient. Neither the 9-AC nor the lipids are soluble in water. A colloidal dispersion consists of at least two discrete phases. The first is a dispersed or internal phase. The second is a continuous or external phase. Systems in the colloidal state contain one or more substances that have at least one dimension in the range of 10–100 Å to a few microns. See pp. 272–4 in Chapter 19, Disperse Systems, *Remington's Pharmaceutical Sciences*, 18th Edition, 1990, Mack Publishing Company, Easton, Pa. 18042. In the colloidal dispersions of the present invention, the dispersed or internal phase comprises particles of 9-AC lipid complex having a particle size in the range of 10 nm to 1000 nm. In selecting the aqueous vehicle, it is recommended to use one having a specific gravity about equal to the lipid complex (est. 1.09 g/cc) to minimize the tendency for the dispersion to separate. The lyophilizate of the lipid complex can be reconstituted with water, saline, or another pharmaceutically acceptable aqueous diluent for intravenous administration. Upon reconstitution a dispersion is obtained which is suitable for injection. The lyophilizate can also be administered orally as an aqueous dispersion or as a paste. While camptothecins are not generally administered subcutaneously because they cause necrosis, it has been observed that the lipid slows the release of the camptothecin into the tissue making it potentially feasible to administer the lipid complex subcutaneously.

For oral administration, the lyophilizate can be reconstituted to form an oral dispersion or formulated into a paste. Alternatively, the lyophilizate can be filled into a soft gelatin capsule for oral administration.

Suitable dosages for 9-AC and camptothecins range from about 35 to 250 mg/m$^2$/hour. The drug is preferably administered as a continuous infusion over 3 to 21 days using programmable continuous infusion ambulatory pump. It is anticipated that the drug will be administered with granulocyte colony stimulating factor (GCSF).

While it is contemplated herein that the lipid/camptothecin complex will be lyophilized to enhance its stability, it will be appreciated that the lipid/camptothecin complex is pharmaceutically active and can be formulated into a dosage form for oral, intravenous or subcutaneous administration without lyophilization. Formulation aids such as antibacterials and antioxidants can be used to enhance the stability of the complex.

The invention will now be described in more detail with reference to the following non-limiting examples.

EXAMPLES 1–8

Lyophilizates of 9-AC were prepared using solvents, phospholipids and excipients in the amounts shown in Table 1. In each case, solutions were prepared by dissolving 9-AC in the amounts shown in DMSO, and, dissolving DMPC and DMPG in chloroform. The solutions were mixed and water for injection was added. The resulting dispersions were stirred for about one hour and chloroform was removed by sparging with nitrogen for about 95 min. DMSO was removed by centrifuging the dispersion, removing the supernatant, and re-suspending the "plug" in water for injection. (In some examples, Millipore or AG Technology tangential flow filters were used to remove DMSO.)

An aqueous solution of the excipient was then added to the dispersion and the dispersion was homogenized using a ULTRA TURREX homogenizer operating at approximately 10,000 rpm, and room temperature. The homogenates were then lyophilized using the protocol described above or a similar process.

The lyophilizate obtained in Example 1 was placed on stability testing at 4° C., 27° C., and 37° C. The initial assay showed 0.299 mg 9-AC per vial. the results of the study to date are shown in Table 2.

TABLE 2

| | Percent Initial Assay | | |
|---|---|---|---|
| | 4° C. | 27° C. | 37° C. |
| 1 week | 99.3 | 97.7 | 99.7 |
| 2 weeks | 100.3 | 103.3 | 104.3 |
| 1 month | 103.7 | 97.7 | 102.3 |
| 2 months | 101 | 102.3 | 102.3 |
| 5 months | 106.4 | 105.7 | 104.7 |
| 7 months | 106.4 | 104.2 | — |

The results of the study show no evidence of deterioration in the lyophilizate of the lipid/camptothecin complex.

EXAMPLE 9

Studies in animals have shown that the lyophilizates of 9-AC of the present invention exhibit antitumor activity in vivo. Colloidal dispersions of the lyophilizate were prepared by dispersing 1 mg of the lyophilizate of Example 6 above in 10 ml of water for injection. The dispersions were evaluated against the HT29 human colon tumor xenograft in female athymic mice. Both intravenous and oral administrations were used. Tumor xenografts were allowed to grow to about 200 mg before initiation of chemotherapy. The size of the tumor was determined based on tumor volume. Treatment comparisons were based on time (days) to three tumor doublings (TTTD). The results are summarized in the Table 3. A high level of citrate was present in the formulation during the first course of treatment and resulted in a high incidence of vehicle-related mortality at the highest I.V. dose levels. The formulation was orally active on a Q2Dx14 schedule with no toxicity.

TABLE 3

| I.V. and P.O. Activity of 9-AC vs. HT29 Xenograft | | | |
|---|---|---|---|
| | CDF | | |
| Schedule | mg/kg Dose | TTTD | Deaths |
| I.V. Bolus | 0 | 26.8 | 0 |
| Q4Dx6 | 1.8 | 34.2 | 0 |

TABLE 1

| Example No. | 1 | 2 | 3 | 4 | 5 | 6 | 7 | 8 |
|---|---|---|---|---|---|---|---|---|
| 9-AC | 0.4 mg | 0.4 mg | 0.4 mg | 0.4 mg | 0.4 mg | 0.4 mg | 0.2 mg | 0.2 mg |
| DMSO | 0.01 ml | 0.01 ml | 0.01 ml | 8.7 ml | 8.7 ml | 10 ml | 5 ml | 5 ml |
| DMPC | 26 mg | 24.2 mg | 3.0 mg | 22.4 mg | 22.4 mg | 22.4 mg | 11.2 mg | 8 mg |
| DMPG | 11.3 mg | 10.4 mg | 1.25 mg | 9.6 mg | 9.6 mg | 9.6 mg | 4.8 mg | 8 mg |
| Chloroform | 0.25 ml | 0.25 ml | 0.31 ml | 0.2 ml | 0.2 ml | 0.2 ml | 0.1 mg | 0.1 ml |
| Mannitol | 15.1 mg | 14.55 mg | 14 mg | 15 mg | 15 mg | 20 mg | 20 mg | 20 mg |
| Sodium Citrate | | | | | 8.9 mg | 8.9 mg | | |
| Citric Acid | | | | | 14.7 mg | 14.7 mg | | |
| WFI | | | | | | | | |
| Lyophilizate | 0.4 mg/vial | 0.4 mg/vial | 0.4 mg/vial | 0.2 mg/vial | 0.2 mg/vial | 2 mg/vial | 1 mg/vial | |

TABLE 3-continued

I.V. and P.O. Activity of 9-AC vs. HT29 Xenograft

| | CDF | | |
|---|---|---|---|
| Schedule | mg/kg Dose | TTTD | Deaths |
| (6 doses) | 2.7 | 38.9 | 2[a] |
| | 4.0 | 25.3 | 6[a] |
| I.V. Bolus | 0 | 26.3 | 0 |
| QDx4 | 0.9 | 35.4 | 0 |
| Days 12, 19, 26 | 1.33 | 46.4[c] | 2[b] |
| (12 doses) | 2.0 | 50.9 | 7[b] |
| P.O. | 0 | 27.0 | 0 |
| Q2Dx14 | 0.67 | 35.6 | 0 |
| | 1.0 | 33.7 | 0 |
| | 1.5 | 42.8 | 0 |

CDF = Collidal dispersion formulation (lipid formulation);
TTTD = Time (days) to 2 × doubling of tumor size
Start Treatment Day 12 for I.V., Day 13 for P.O.;
N = 10/group
[a]First dose of CDF contained citrate buffer. Most deaths attributed to vehicle. Second and remaining doses were citrate-free
[b]First course of DMSO/intralipid contained citrate buffer. Most deaths attributed to vehicle. Second and third courses were citrate-free
[c]1 partial regression Having described the invention in detail and by reference to preferred embodiments thereof, it will be apparent that modifications and variations are possible without departing from the scope of the invention defined in the appended claims.

What is claimed is:

1. A pharmaceutical composition comprising a lyophilizate of a non-liposomal complex of a water insoluble camptothecin and a phospholipid, said lyophilizate additionally containing a pharmaceutically acceptable lyophilization excipient, wherein the weight ratio of said camptothecin to said phospholipid in said composition is about 1:80 to 1:5.

2. The composition of claim 1 wherein said composition forms a colloidal dispersion when reconstituted with a physiologically acceptable aqueous diluent.

3. The composition of claim 2 wherein the diluent has a specific gravity approximately equal to the lipid complex.

4. The composition of claim 1 wherein said phospholipid is selected from the group consisting of dimyristoylphosphatidyl choline, dimyristoylphosphatidyl glycerol, dipalmitoyliphosphatidyl choline, dipalmitoylphophatidyl glycerol, distearoylphosphatidyl choline, distearoylphosphatidyl glycerol, and any combination thereof.

5. The composition of claim 1 wherein said phospholipid is a mixture of dimyriqtoylphosphatidyl choline and dimyristoylphosphatidyl glycerol.

6. The composition of claim 5 wherein said dimyristoylphosphatidyl choline is present in a weight ratio to said dimyristoylphosphatidyl glycerol of about 7:3.

7. The composition of claim 5 wherein the composition additionally contains cholesterol.

8. The composition of claim 5 wherein said excipient is mannitol.

9. The composition of claim 5 wherein said water insoluble camptothecin is 9-aminocamptothecin.

10. The composition of claim 9 wherein the 9-aminocamptothecin is 9-amino-20-(S)-camptothecin.

11. The composition of claim 9 wherein the 9-aminocamptothecin is 9-amino-20-(R,S)-camptothecin.

12. The composition of claim 1 wherein the composition is suitable for intravenous administration.

13. The composition of claim 1 wherein the composition is suitable for oral administration.

14. The composition of claim 1 wherein the composition is suitable for subcutaneous administration.

15. A non-liposomal lipid complex of a water insoluble camptothecin and a phospholipid, wherein the weight ratio of said camptothecin to said phospholipid in said complex is about 1:80 to 1:5.

16. The complex of claim 15 wherein said phospholipid is selected from the group consisting of dimyristoylphosphatidyl choline, dimyristoylphosphatidyl glycerol, dipalmitoyliphosphatidyl choline, dipalmitoylphophatidyl glycerol, distearoylphosphatidyl choline, distearoylphosphatidyl glycerol, and any combination thereof.

17. The complex of claim 16 wherein said phospholipid is a mixture of dimyristoylphosphatidyl choline and dimyristoylphosphatidyl glycerol.

18. The complex of claim 17 wherein said dimyristoylphosphatidyl choline is present in a weight ratio to said dimyristoylphosphatidyl glycerol of about 7:3.

19. The complex of claim 15 wherein said water insoluble camptothecin is 9-aminocamptothecin.

20. The complex of claim 19 wherein the 9-aminocamptothecin is 9-amino-20(S)-camptothecin.

21. The composition of claim 19 wherein the 9-aminocamptothecin is 9-amino (R,S)-camptothecin.

* * * * *